(12) United States Patent
Huerta

(10) Patent No.: US 10,220,174 B2
(45) Date of Patent: Mar. 5, 2019

(54) SEPTI-CANNULA

(71) Applicant: Christine M. Huerta, Tampa, FL (US)

(72) Inventor: Christine M. Huerta, Tampa, FL (US)

( * ) Notice: Subject to any disclaimer, the term of this patent is extended or adjusted under 35 U.S.C. 154(b) by 514 days.

(21) Appl. No.: 15/045,300

(22) Filed: Feb. 17, 2016

(65) Prior Publication Data

US 2017/0232220 A1    Aug. 17, 2017

(51) Int. Cl.
*A61M 16/06* (2006.01)
*A61M 16/08* (2006.01)

(52) U.S. Cl.
CPC .... *A61M 16/0672* (2014.02); *A61M 16/0605* (2014.02); *A61M 16/085* (2014.02); *A61M 16/0875* (2013.01)

(58) Field of Classification Search
None
See application file for complete search history.

(56) References Cited

U.S. PATENT DOCUMENTS

| | | | |
|---|---|---|---|
| 5,113,857 A * | 5/1992 | Dickerman | A61M 16/0666 128/206.11 |
| 5,794,619 A * | 8/1998 | Edelman | A61M 16/0666 128/200.24 |
| 6,422,240 B1 | 7/2002 | Levitsky | |
| 6,645,172 B1 | 11/2003 | Gueret | |
| 7,383,839 B2 | 6/2008 | Porat | |
| 7,406,966 B2 | 8/2008 | Wondka | |
| 8,573,219 B2 | 11/2013 | Wondka | |
| 2002/0046755 A1 * | 4/2002 | De Voss | A61M 16/0666 128/207.18 |
| 2002/0112730 A1 * | 8/2002 | Dutkiewicz | A61M 16/0666 128/207.18 |
| 2005/0161049 A1 | 7/2005 | Wright | |
| 2008/0167676 A1 | 7/2008 | Howard | |
| 2008/0190436 A1 * | 8/2008 | Jaffe | A61M 16/0666 128/207.18 |
| 2009/0173350 A1 | 7/2009 | Swanson | |
| 2011/0067704 A1 * | 3/2011 | Kooij | A61M 16/0666 128/207.18 |
| 2014/0276169 A1 | 9/2014 | Chua | |
| 2016/0051787 A1 * | 2/2016 | Matsubara | A61M 16/0672 128/205.25 |

FOREIGN PATENT DOCUMENTS

| | | | | |
|---|---|---|---|---|
| WO | WO 03068301 A1 * | 8/2003 | | A61M 16/0666 |
| WO | WO 2015121815 A1 * | 8/2015 | | B29C 45/36 |
| WO | WO 2015156690 A1 * | 10/2015 | | A61M 16/16 |
| WO | WO-2015156690 A1 * | 10/2015 | | A61M 16/16 |
| WO | PCTUS1713327 | 8/2017 | | |

* cited by examiner

*Primary Examiner* — Kathryn E Ditmer
(74) *Attorney, Agent, or Firm* — Christopher M. Ramsey; GrayRobinson, P.A.

(57) ABSTRACT

A nasal cannula including a manifold having a delivery channel and a collection channel fluidly connected to a delivery nasal prong for delivering a gas to be inhaled from a patient's nose and to a collection prong for collecting gas exhaled from the patient's nose. The prongs are composed of a resilient material having sufficient memory that allows the prongs to be resiliently spread apart to be inserted into the respective nares of the patient's nose and when released, gently grasp the columella of the patient's nose to secure the cannula in position. The prongs are oriented leftwardly or rightwardly of the channels so that the right or left portions of the patient's face remain unobscured during surgery.

12 Claims, 8 Drawing Sheets

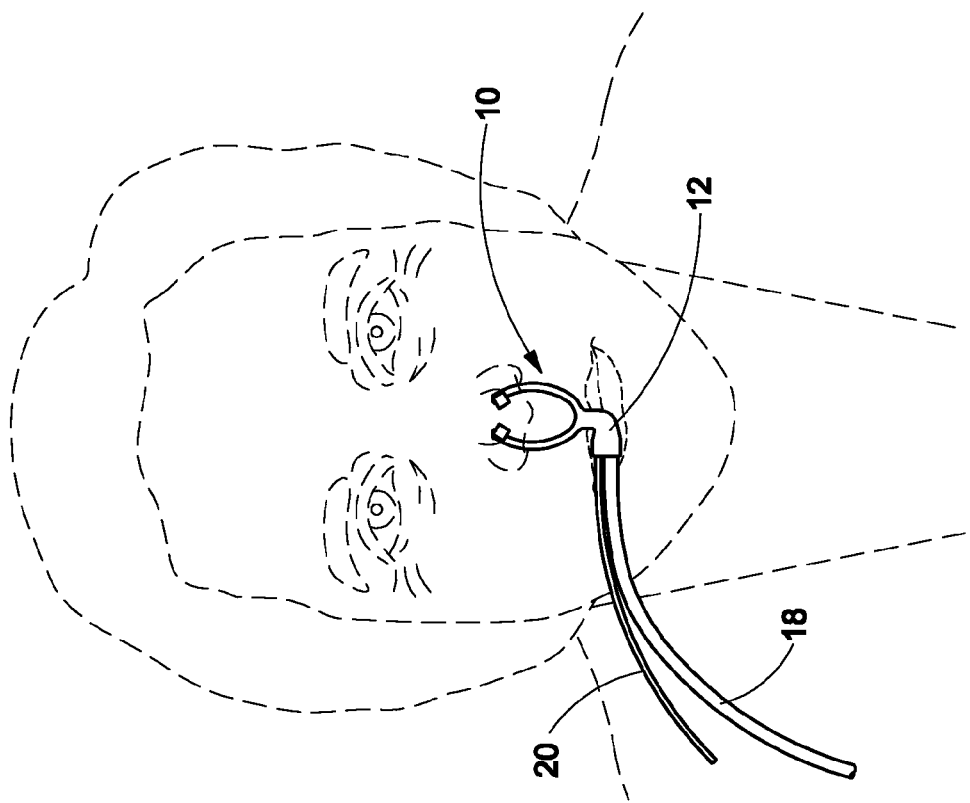
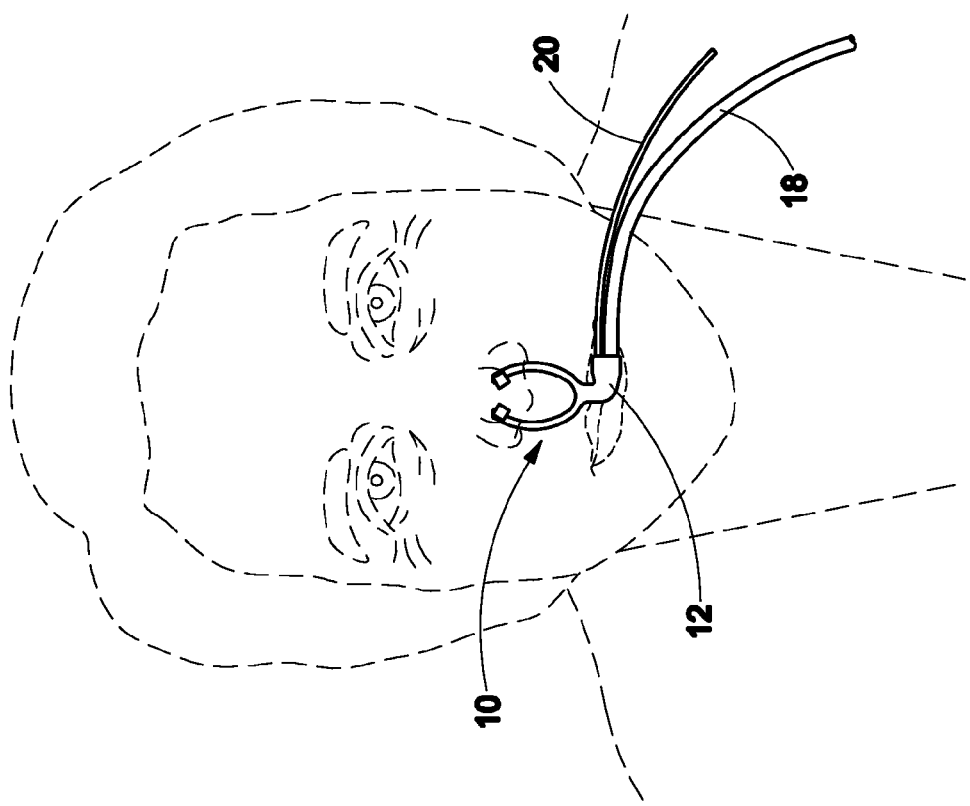

SEPTI-CANNULA

BACKGROUND OF THE INVENTION

Field of the Invention

This invention relates to nasal cannulas. More particularly, this invention relates to nasal cannulas that deliver oxygen to a patient's nose and sampling of carbon dioxide being exhaled from the patient's nose.

Description of the Background Art

Representative nasal cannulas for the delivery of oxygen to the patient's nose include two nasal prongs fluidly connected to an oxygen-delivery tube (as used herein the term "patient" refers to humans as well as animals). The nasal prongs are inserted into the patient's nose and held into position by draping the respective oxygen-delivery tubes over the patient's ears. The tubes are typically joined anteriorly under the patient's chin (or behind the patient's head) by a tube clasp encircling both of the tubes. The tube clasp may be slid upwardly toward the patient's ears to take up any slack in the tubes so that the nasal prongs are forcibly held in the patient's nostrils. The sliding tube clasp may alternatively be slid downwardly along the tubes to create slack in the tubes and thereby lessen the degree of pressure exerted on the patient's nostrils. Alternatively, as shown in U.S. Pat. Nos. 8,573,219 and 7,406,966, the disclosures of both of which are hereby incorporated by reference herein, the nasal cannula may be held in position in the patient's nose by a coupler that pinches the nasal prongs onto the columella of the nose.

Improved delivery/sampling nasal cannulas are designed to deliver oxygen to a patient's nose and to sample exhausted carbon dioxide from the patient's nose. Representative delivery/sampling nasal cannulas typically comprise two nasal prongs for insertion into the nostrils of the patient. One prong is fluidly connected to a delivery tube for delivery of oxygen into one flare of the patient and the other prong is fluidly connected to a collection tube for the collection of the exhaled gases to be monitored, typically end tidal carbon dioxide, from the other nare of the patient. For example, the collection tube may be fluidly connected to a capnograph for gas analysis.

Prior art delivery/sampling nasal cannulas typically secure the nasal prongs in the patient's nostrils by draping the delivery tube around one of the patient's ears and draping the collection tube around the patient's other ear. The delivery tube and the collection tube are typically joined anteriorly under the patient's chin (or behind the patient's head) by a tube clasp encircling both of the tubes that allows for tightening or loosening of the nasal prongs in the patient's nose. Representative U.S. Pat. Nos. include 7,383,839 and 6,422,240, the disclosures of both of which are hereby incorporated by reference herein.

During a surgical procedure to the patient's face, many times a prior art nasal cannula must be manually manipulated to avoid the surgical site. For example, if the surgeon is operating on the patient's right cheek, the tube extending from the nasal prong in the patient's right nare over the patient's right ear, must be moved and secured away from the patient's right cheek. Typically this involves loosening the right tube so that it can be moved upwardly (or downwardly) away from the surgical site and then taped to the patient's face away from the surgical site. However, the patient's face, having been prepped with a solution to render the surgical site clean and sterile, compromises the ability for the tape to adhere to the face, sometimes resulting in the tube coming loose and obstructing the surgical site. The loosened tube may also pull one or both of the nasal prongs from the patient's nostrils.

Therefore, an object of this invention to provide an improvement which overcomes the aforementioned inadequacies of the prior art devices and provides an improvement which is a significant contribution to the advancement of the nasal cannula art.

Another object of this invention is to provide a delivery/sampling nasal cannula to deliver oxygen to a patient's nose via a delivery tube and to sample exhausted gases from the patient's nose via a collection tube.

Another object of this invention is to provide a nasal cannula whose tubes are both oriented unidirectionally, either both leftwardly or both rightwardly, from the patient's nostrils such that the right or left, respectively, area of the patient's face remains free of the tubes.

Another object of this invention is to provide a delivery/sampling nasal cannula whose delivery and collection tubes are both oriented unidirectionally.

Another object of this invention is to provide a delivery/sampling nasal cannula whose delivery and collection tubes are both fluidly connected to both of the nostrils such that oxygen is delivered to both nares and exhausted air is sampled from both of the nares.

Another object of this invention is to provide a delivery/sampling nasal cannula that precludes an interruption in oxygen delivery and measurement of ETCO2 during the surgical procedure due to secure placement of the cannula to the columella.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

For the purpose of summarizing this invention, this invention comprises a delivery/sampling nasal cannula to deliver oxygen to a patient's nose via a delivery tube and to sample exhausted gases from the patient's nose via a collection tube. The tubes are both oriented unidirectionally, either both leftwardly or both rightwardly, from the patient's nostrils such that the right or left, respectively, area of the patient's face remains free of the tubes and therefore do not obstruct or interfere with surgery. In a first embodiment, the delivery and collection tubes are fluidly connected to respective nares of the patient's nose such that oxygen is delivered to one nare and exhausted carbon dioxide is collected from the other nare. In a second embodiment, the delivery and collection tubes are both fluidly connected to both of the nares such that oxygen is delivered to both nares and exhausted air is sampled from both of the nares.

An important feature of both embodiments of the nasal cannula of the invention is the unidirectional orientation of tubes to be oriented rightwardly or leftwardly when inserted into the patient's nose such that the delivery and collection tubes extend unidirectionally in the same direction. In this manner, if for example the surgical site is the patient's left cheek area, the nasal cannula may be oriented rightwardly so that the tubes extend rightwardly and do not obstruct or otherwise compromise the surgical site on the patient's left cheek. Conversely, if for example the surgical site is the patient's right cheek area, the nasal cannula may be oriented leftwardly so that the tubes extend leftwardly and do not obstruct or otherwise compromise the surgical site on the patient's right cheek. Advantageously, due to secure placement of the cannula to the columella, the use of the nasal cannula of the invention will assure that the patient will not have an interruption in oxygen delivery and measurement of ETCO2 during the surgical procedure.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIGS. 6A and 6B are front elevational views showing the nasal cannula oriented rightwardly and leftwardly, respectively;

Similar reference characters refer to similar parts throughout the several views of the drawings.

DETAILED DESCRIPTION OF THE PREFERRED EMBODIMENTS

The first embodiment of the nasal cannula 10 of the invention is disclosed in FIGS. 1-6 whereas the second embodiment is disclosed in FIGS. 7-13.

Figure 1:
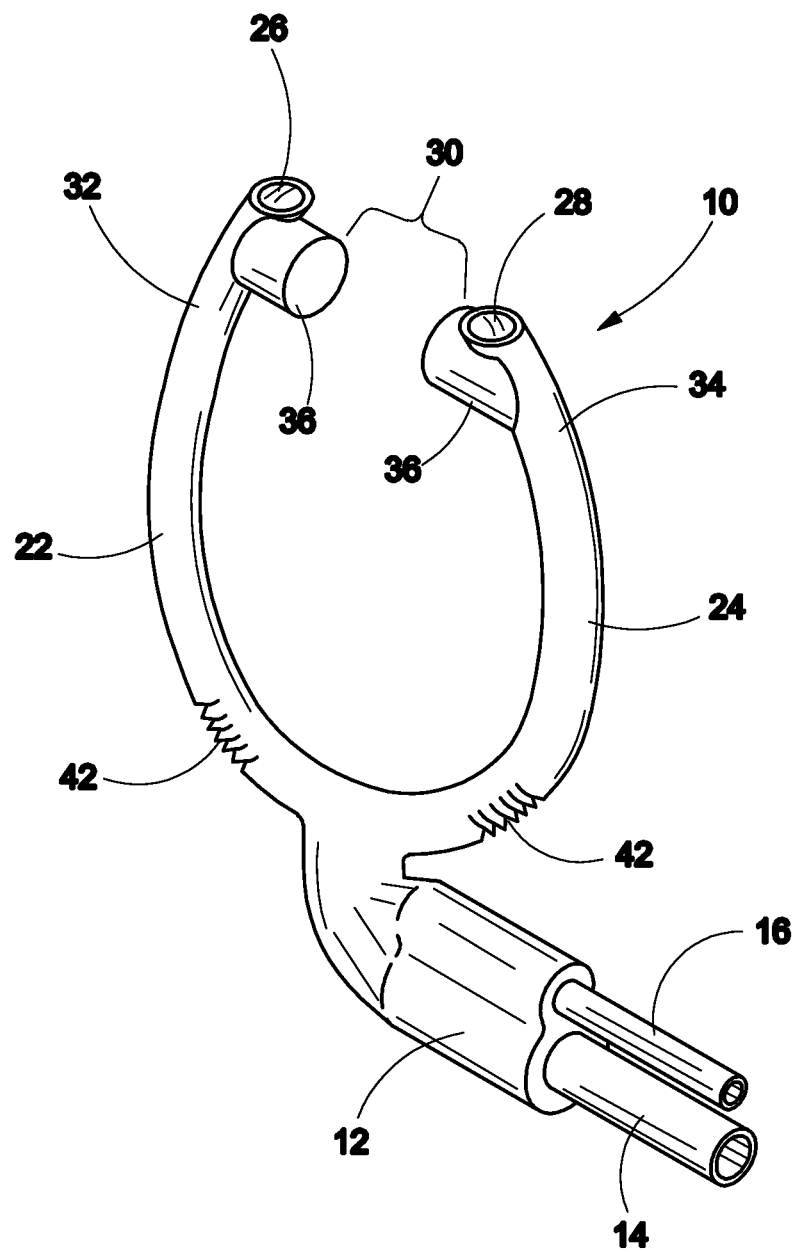
FIG. 1 is a perspective view of the first embodiment of the nasal cannula of the invention.
Figure 3:
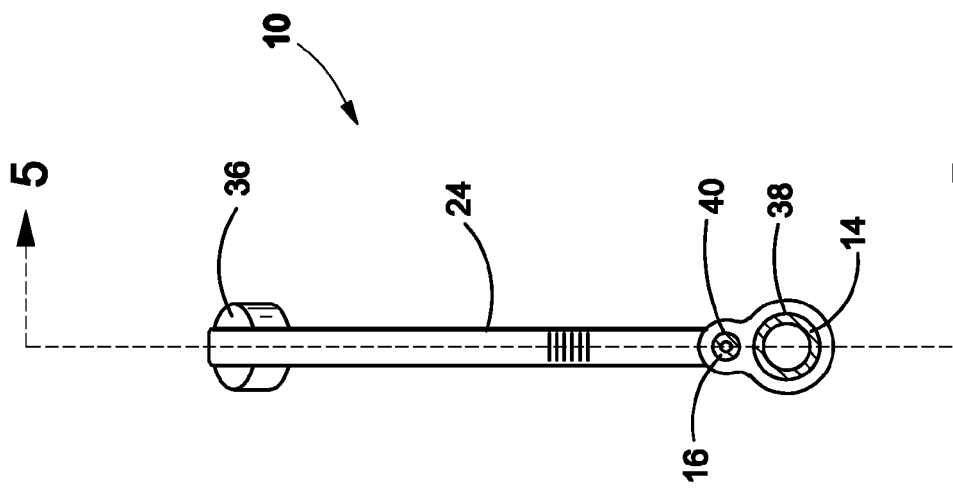
FIG. 3 is a left elevational view thereof.
Figure 2:
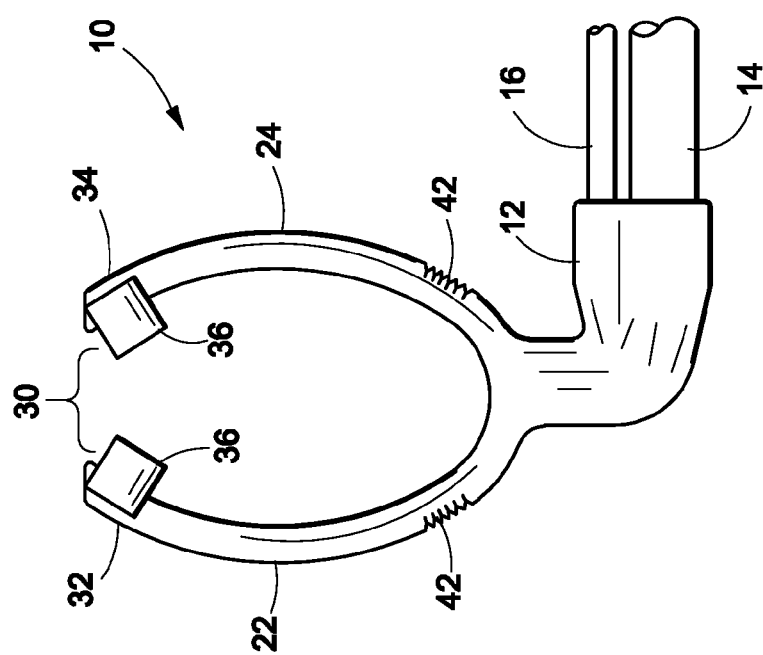
FIG. 2 is a front elevational view thereof.
Figure 4:
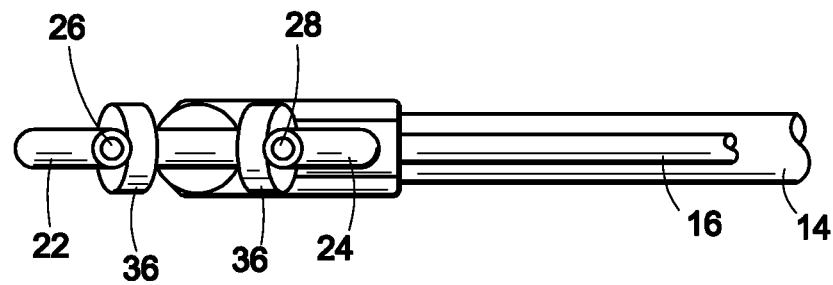
FIG. 4 is a top elevational view thereof.
Figure 5:
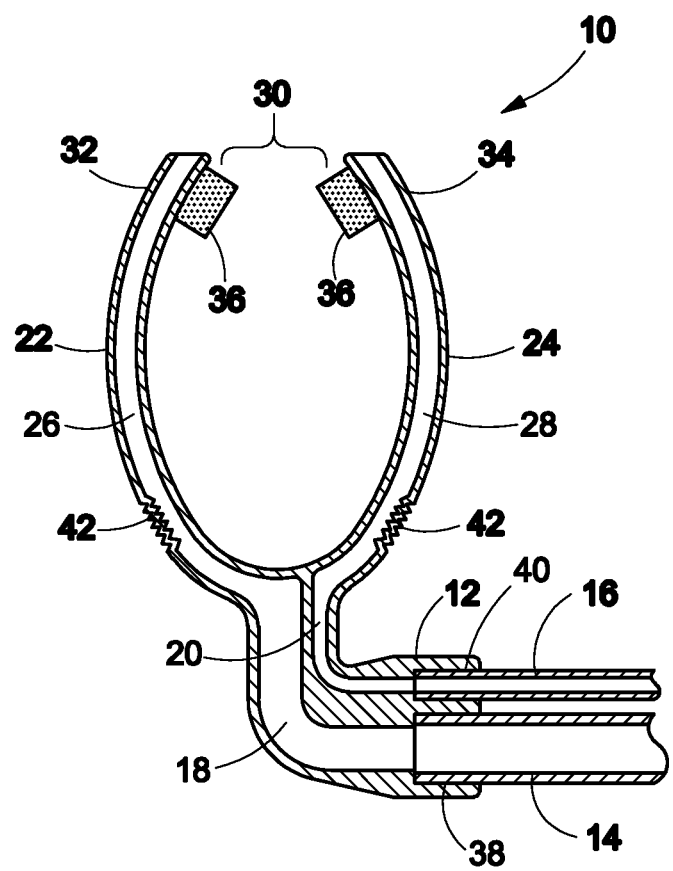
FIG. 5 is a cross-sectional view of FIG. 3 along lines 5-5.
Figure 7:
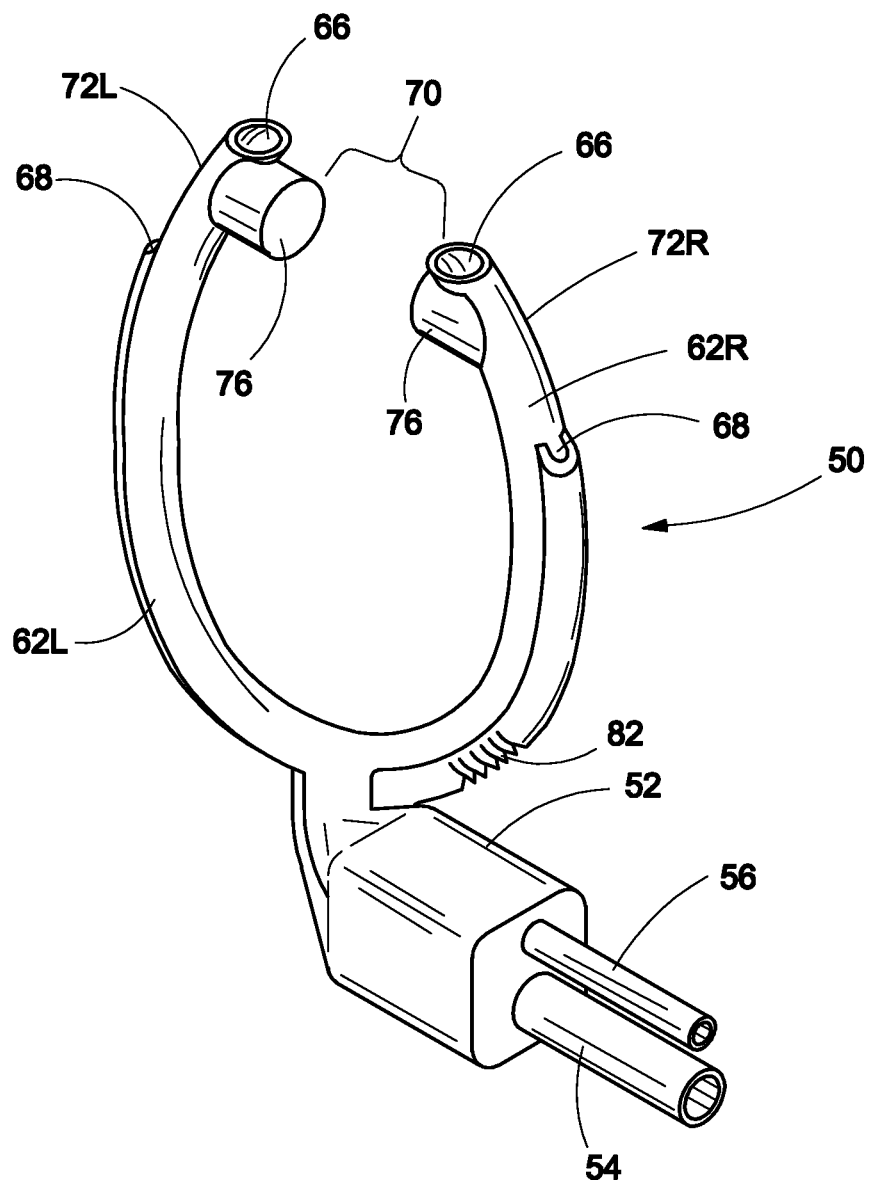
FIG. 7 is a perspective view of the second embodiment of the nasal cannula of the invention.
Figure 9:
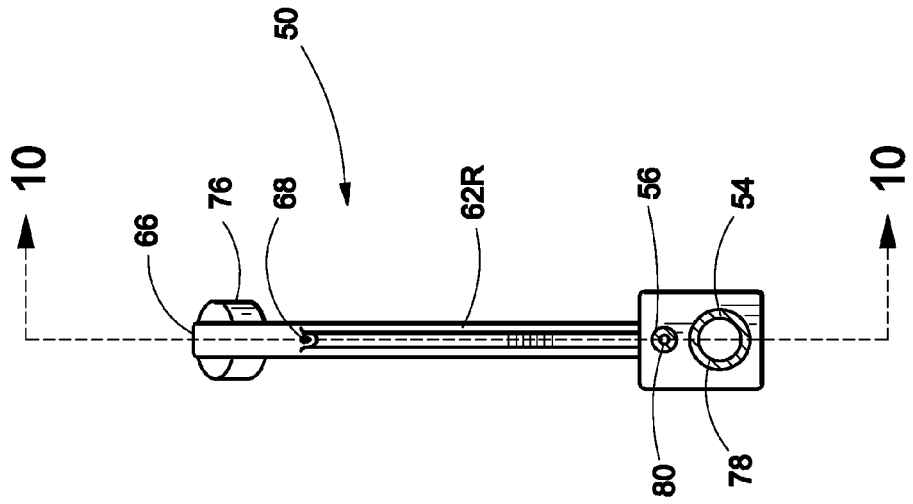
FIG. 9 is a left elevational view thereof.
Figure 8:
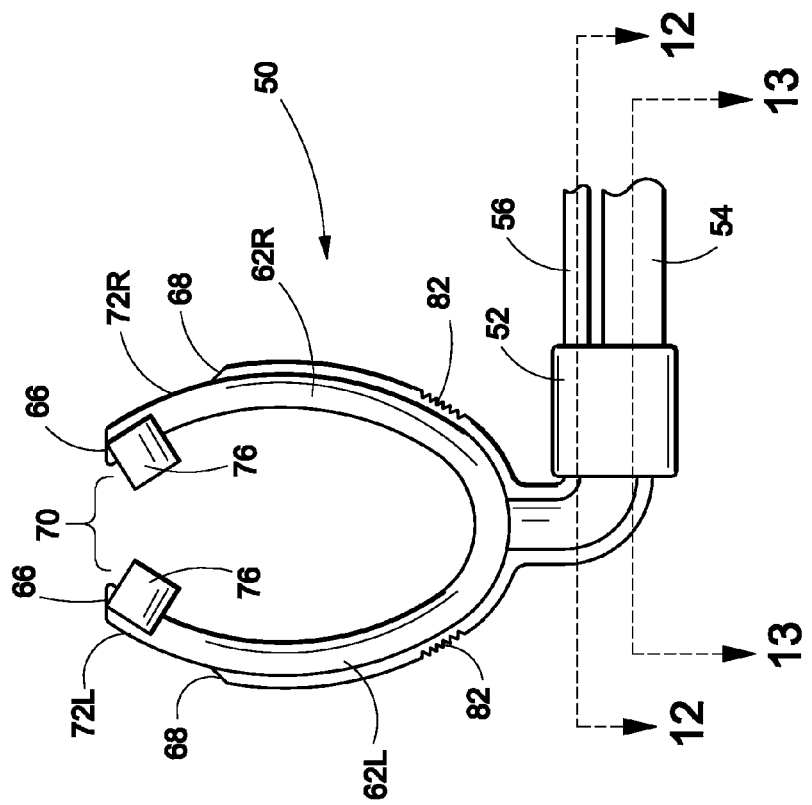
FIG. 8 is a front elevational view thereof.

In the first embodiment of FIGS. 1-6, the nasal cannula 10 comprises a manifold 12 having a delivery channel 18 and a collection channel 20 respectively fluidly connected to a delivery tube 14 and a collection tube 16 (see FIG. 5). The delivery channel 18 and the collection channel 20 of the manifold 12 are also fluidly connected to a delivery nasal prong 22 and a collection nasal prong 24, respectively. The channels 18 and 20 in the manifold 12 are both curvilinear at approximately ninety degrees such that the tubes 14 & 16 and the prongs 22 & 24 are oriented approximately 90 degrees relative to one another.

The delivery and collection nasal prongs 22 and 24 comprise internal delivery and collection channels 26 and 28, respectively. The delivery and collection prongs 22 and 24 preferably each comprise an arcuate configuration facing one another to define a space 30 between the respective ends 32 and 34 thereof. The prongs 22 and 24 are composed of a resilient material having sufficient memory that allows the prongs 22 and 24 to be resiliently spread apart to increase the space 30 allowing the ends 32 and 34 to be inserted into the respective nares of the patient's nose. When released, the material's resilient memory moves the ends 32 and 34 toward their original at-rest position to gently grasp the columella. It is noted that comfort pads 36 may be provided on the facing surfaces of the ends 32 and 34 for added comfort.

In operation, a gas such as oxygen may be delivered through the delivery tube 14, then through the delivery channel 18 of the manifold 12, then through the delivery channel 26 of the delivery nasal prong 22 into the nare in which the delivery nasal prong 22 is inserted. Exhaust gas from the patient, such as carbon dioxide, may be collected from the nare in which the collection nasal prong 24 is inserted by flowing through the collection channel 28 of the collection nasal prong 24, then through the collection channel 20 of the manifold 12 and then through the collection tube 16.

Preferably, the manifold 12 and the nasal prongs 22 and 24 are one-piece injection molded with their respective channels 18 & 20 and 22 & 24. Also preferably, during assembly during manufacturing, the delivery and collection tubes 14 and 16 are solvent-welded into annular seats 38 and 40 formed in the manifold 12.

Optionally, one or both of the nasal prongs 22 and 24 may include a living hinge 42 facing outwardly, such as an area composed of an accordion-shaped wall, that allows easier resilient spreading of the nasal prongs 22 and 24 apart so they can be more easily spread apart for insertion into the patient's nose and yet still have sufficient resiliency when released to grasp the columella with sufficient force to preclude them from inadvertent releasing the columella during surgery.

Importantly, as shown in FIGS. 6A and 6B, the nasal cannula 10 of the invention may be oriented rightwardly (FIG. 6A) or leftwardly (FIG. 6B) when inserted into the patient's nose such that the delivery and collection tubes 14 and 16 extend unidirectionally in the same direction. In this manner, if for example the surgical site is the patient's left cheek area, the nasal cannula 10 may be oriented rightwardly (FIG. 6A) so that the tubes 14 and 16 extend rightwardly and do not obstruct or otherwise compromise the surgical site on the patient's left cheek. Conversely, if for example the surgical site is the patient's right cheek area, the nasal cannula 10 may be oriented leftwardly (FIG. 6B) so that the tubes 14 and 16 extend leftwardly and do not obstruct or otherwise compromise the surgical site on the patient's right cheek.

Figure 10:
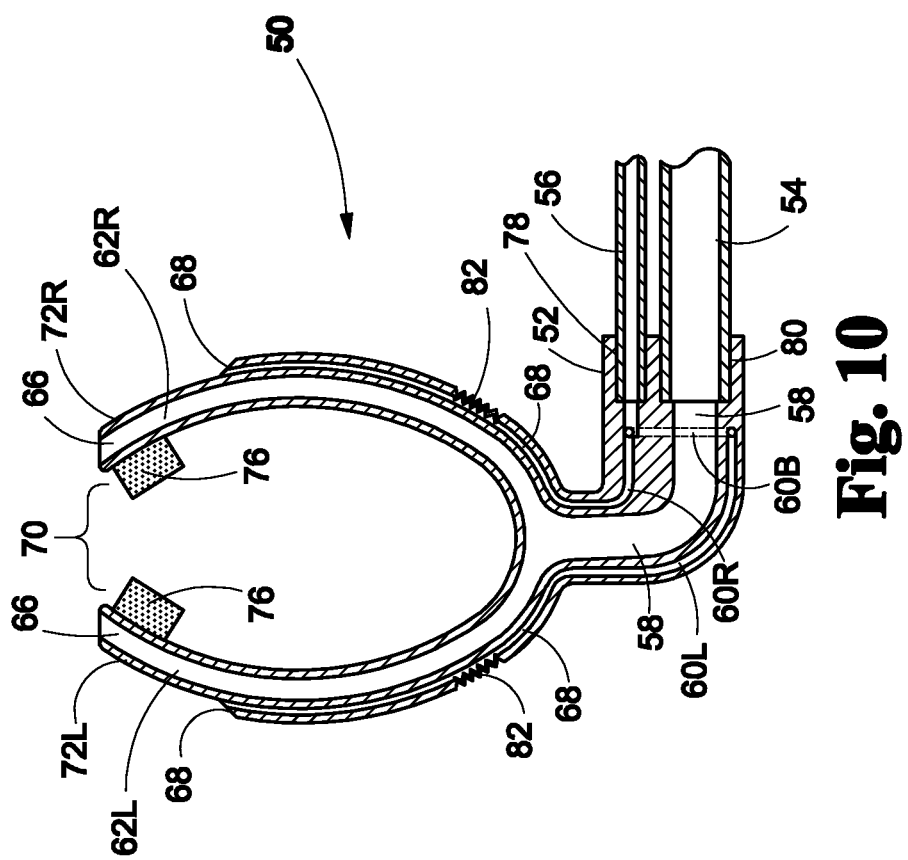
FIG. 10 is a cross-sectional view of FIG. 9 along lines 10-10 of FIG. 9.
Figure 11:
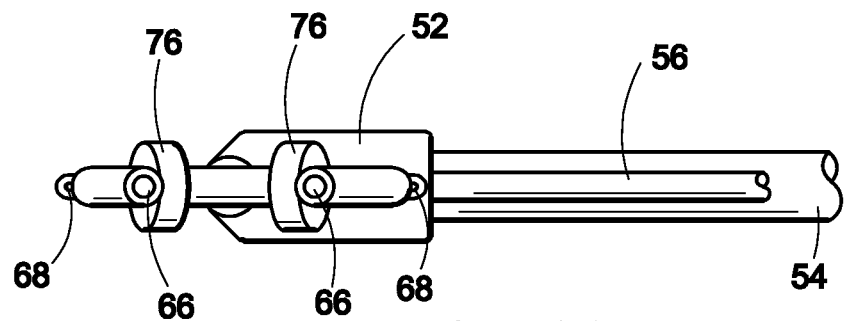
FIG. 11 is a top elevational view thereof.
Figure 12:
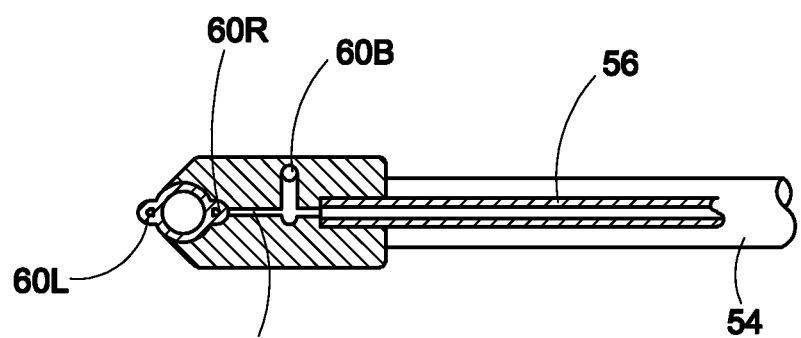
FIG. 12 is a cross-sectional view of FIG. 8 along lines 12-12.
Figure 13:
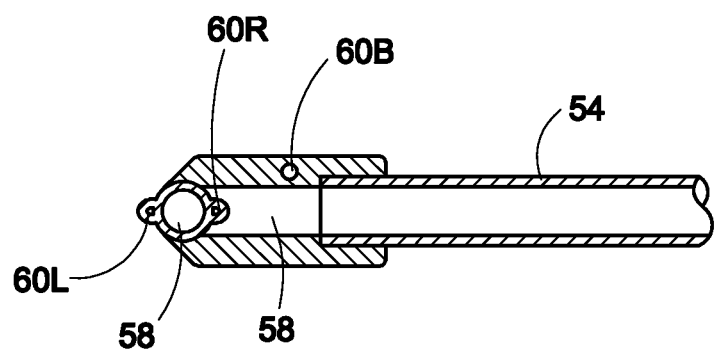
FIG. 13 is a cross-sectional view of FIG. 8 along lines 13-13.

Turning now to the second embodiment of the nasal cannula 50 of the invention shown in FIGS. 7-13, the nasal cannula 10 comprises a manifold 52 having a delivery channel 58 and a pair of right and left collection channels 60R and 60L respectively fluidly connected to a delivery tube 54 and a collection tube 56 (see FIG. 10).

More specifically, the right collection channel 60R preferably extends on the right side of the manifold 52 whereas the left collection channel 60L preferably extends on the left side of the manifold 52. The right and left collection channels 60R and 60L are fluidly connected together by a bypass channel 60B extending transversely through the manifold 52. When the collection tube 56 is directly connected to the right collection channel 60R, it is also indirectly fluidly connected via the bypass channel 60B to the left collection channel 60L.

The delivery channel 58 and the left and right collection channels 60L and 60R of the manifold 52 are fluidly connected to a left nasal prong 62L and a right nasal prong 62R respectively. The delivery channel 58 and the collection channels 60L and 60B in the manifold 52 are curvilinear at approximately ninety degrees such that the tubes 54 & 56 and the prongs 62l, & 62R are oriented approximately 90 degrees relative to one another.

The left and right nasal prongs 62L & 62R each comprise an internal delivery channel 66 and an external collection channel 68 formed on the outside of the prong 62L & 62R. The external collection channels 68 may extend to the respective ends 72L & 72R of the prongs 62L & 62R; however, preferably they stop an appreciable distance from the respective ends 72L & 72R of the prongs 62L & 62R as shown in FIG. 10.

The prongs 62L & 62R preferably each comprise an arcuate configuration facing one another to define a space 70 between the respective ends 72L & 72R thereof. As in the first embodiment, the prongs 62L & 62R are composed of a resilient material having sufficient memory that allows the prongs 62L & 62R to be resiliently spread apart to increase the space 70 allowing the ends 72L & 72R to be inserted into the respective nares of the patient's nose. When released, the material's resilient memory moves the ends 72L & 72R toward their original at-rest position to gently grasp the columella. It is noted that comfort pads 76 may be provided on the facing surfaces of the ends 72L & 72R for added comfort.

in operation, a gas such as oxygen may be delivered through the delivery tube 54, then through the delivery channel 58 of the manifold 52, then through the delivery channel 66 of the nasal prongs 62L & 62R into the nares. Exhaust gas from the patient, such as carbon dioxide, may be collected from the nares by flowing through the collection channel 68 of the nasal prongs 62L & 62R, then through the collection channels 60L &60R and the bypass channel 60B of the manifold 12 and then through the collection tube 56.

Preferably, as in the case of the first embodiment, the manifold 52 and the nasal prongs 62L & 62R are one-piece injection molded with their respective channels 58 and 60. Also preferably, during assembly during manufacturing, the delivery and collection tubes 54 and 56 are solvent-welded into annular seats 78 and 80 formed in the manifold 52.

Optionally, as in the case of the first embodiment, one or both of the nasal prongs 62L & 62R may include a living hinge 82 facing outwardly, such as an facing area composed of an accordion-shaped wall, that allows easier resilient spreading of the nasal prongs 62L & 62R apart so they can be more easily spread apart for insertion into the patient's nose and yet still have sufficient resiliency when released to grasp the columella with sufficient force to preclude them from inadvertent releasing the columella during surgery.

Importantly, as in the case of the first embodiment, the nasal cannula 50 of the invention may be oriented rightwardly or leftwardly when inserted into the patient's nose such that the delivery and collection tubes 54 and 56 extend unidirectionally in the same direction. In this manner, if for example the surgical site is the patient's left cheek area, the nasal cannula 50 may be oriented rightwardly so that the tubes 54 and 56 extend rightwardly and do not obstruct or otherwise compromise the surgical site on the patient's left cheek. Conversely, if for example the surgical site is the patient's right cheek area, the nasal cannula 50 may be reversed and oriented leftwardly so that the tubes 54 and 56 extend leftwardly and do not obstruct or otherwise compromise the surgical site on the patient's right cheek.

It should be appreciated that since the nasal cannula 10 & 50 is reversible, references to "left" and "right" throughout the Specification and the claims are for convenience only and are not limiting to the structure or operation of either embodiments of the nasal cannula 10 & 50.

The present invention includes that contained in the appended claims as well as that of the foregoing description. Although this description has been described in its preferred form with a certain degree of particularity, it should be understood that the present disclosure of the preferred form has been made only by way of example and that numerous changes in the details of construction, combination, or arrangement of parts thereof may be resorted to without departing from the spirit and scope of the invention.

Now that the invention has been described,

What is claimed is:

1. A nasal cannula comprising in combination:
    a delivery channel and a collection channel respectively in fluid communication with a delivery tube for delivering a gas to be inhaled from a patient's nose and a collection tube for collecting gas exhaled from the patient's nose;
    a delivery nasal prong and a collection nasal prong respectively fluidly connected to said delivery channel and collection channel, said channels being curvilinear at approximately ninety degrees such that the tubes and said prongs extend approximately ninety degrees relative to one another; and
    said delivery and collection nasal prongs respectively comprising internal delivery and collection channels and comprising an arcuate configuration facing one another to define a space between respective ends thereof, said prongs being composed of a resilient material having sufficient memory that allows said prongs to be resiliently spread apart to increase said space allowing said ends to be inserted into the respective nares of the patient's nose and when released, move said ends to gently grasp a columella of the patient's nose,
    wherein at least one of said nasal prongs includes a living hinge that allows easier resilient spreading of said nasal prongs apart so they can be more easily spread apart for insertion into the patient's nose and yet still have sufficient resiliency when released to grasp the columella with sufficient force to preclude them from inadvertent releasing the columella during surgery.

2. The nasal cannula as set forth in claim 1, further including comfort pads on facing surfaces of said ends.

3. The nasal cannula as set forth in claim 1, wherein said delivery channel and collection channel are within a manifold and said manifold and nasal prongs are one-piece injection molded with their respective said channels.

4. The nasal cannula as set forth in claim 3, wherein the delivery and collection tubes are solvent-welded into annular seats formed in said manifold.

5. The nasal cannula as set forth in claim 1, wherein said living hinge faces outwardly and comprises an accordion-shaped wall.

6. A nasal cannula comprising in combination:

a manifold having a delivery channel and a first collection channel for respective fluid connection to a delivery tube and a collection tube;

a left nasal prong and a right nasal prong, at least one of the left nasal prong and right nasal prong being fluidly connected to said delivery channel and at least one of the left nasal prong and right nasal prong being fluidly connected to said first collection channel;

said delivery channel and said first collection channel being curvilinear at approximately ninety degrees such that a portion of the delivery channel and first collection channel extend unidirectionally approximately ninety degrees relative to said prongs in such a way that the collection tube and the delivery tube, when respectively connected to said collection channel and delivery channel, are configured to extend over a single cheek of a patient when the left nasal prong and right nasal prong are worn by the patient;

said prongs each comprising an arcuate configuration facing one another to define a space between respective ends thereof, said prongs being composed of a resilient material having sufficient memory that allows said prongs to be resiliently spread apart to increase said space allowing said ends to be inserted into the respective nares of the patient's nose and when released, move said ends to gently grasp the columella; and wherein at least one of said nasal prongs includes a living hinge that allows easier resilient spreading of said nasal prongs apart so they can be more easily spread apart for insertion into the patient's nose and yet still have sufficient resiliency when released to grasp the columella with sufficient force to preclude them from inadvertent releasing the columella during surgery.

7. The nasal cannula as set forth in claim 6, further including comfort pads affixed on facing surfaces of said ends.

8. The nasal cannula as set forth in claim 6, further comprising a second collection channel, wherein said first and second collection channels are fluidly connected together by a bypass channel extending transversely through said manifold such that when the collection tube is directly connected to said first collection channel, the collection tube is indirectly connected via said bypass channel to said second collection channel.

9. The nasal cannula as set forth in claim 6, wherein said left and right nasal prongs each comprise an internal delivery channel and an external collection channel formed on the outside of said prong.

10. The nasal cannula as set forth in claim 6, wherein said manifold and said nasal prongs are one-piece injection molded with their respective said channels.

11. The nasal cannula as set forth in claim 6, further comprising said delivery tube and said collection tube, wherein said delivery and collection tubes are solvent-welded into annular seats formed in said manifold.

12. The nasal cannula as set forth in claim 6, wherein said living hinge faces outwardly and comprises an accordion-shaped wall.

* * * * *